United States Patent [19]

Ogawa et al.

[11] Patent Number: 5,578,340

[45] Date of Patent: *Nov. 26, 1996

[54] MEDICAL MEMBER AND METHOD OF MANUFACTURING THE SAME

[75] Inventors: Kazufumi Ogawa, Hirakata; Norihisa Mino, Settu; Mamoru Soga, Osaka, all of Japan

[73] Assignee: Matsushita Electric Industrial Co., Ltd., Osaka, Japan

[ * ] Notice: The term of this patent shall not extend beyond the expiration date of Pat. No. 5,143,750.

[21] Appl. No.: 485,787

[22] Filed: Jun. 7, 1995

Related U.S. Application Data

[62] Division of Ser. No. 89,629, Jul. 12, 1993, Pat. No. 5,443,511, which is a continuation of Ser. No. 824,314, Jan. 23, 1992, abandoned.

[30] Foreign Application Priority Data

Jan. 28, 1991 [JP] Japan .................................. 3-008323
Feb. 6, 1991 [JP] Japan .................................. 3-038134
Mar. 14, 1991 [JP] Japan .................................. 3-049841

[51] Int. Cl.$^6$ ........................ B05D 3/06; B05D 3/10; B05D 1/36

[52] U.S. Cl. .................. 427/2.1; 427/337; 427/352; 427/387; 427/535

[58] Field of Search ................. 427/2.1, 387, 337, 427/352, 407.1, 535, 299

[56] References Cited

U.S. PATENT DOCUMENTS

| | | | |
|---|---|---|---|
| 3,859,320 | 1/1975 | Atherton | 427/387 |
| 3,950,588 | 4/1976 | McDougal | 427/387 |
| 4,504,228 | 3/1985 | Maetani et al. | 433/199.1 |
| 4,539,061 | 9/1985 | Sagiv . | |
| 4,563,394 | 1/1986 | Ishikawa | 427/391 |
| 4,711,820 | 12/1987 | Arkles et al. | 428/429 |
| 4,761,316 | 8/1988 | Ogawa | 427/131 |
| 4,833,093 | 5/1989 | Malmqvist et al. | 427/255.6 |
| 4,863,794 | 9/1989 | Fujii et al. | 428/325 |
| 4,985,273 | 1/1991 | Mino | 427/130 |
| 4,997,684 | 3/1991 | Franz et al. | 427/387 |
| 5,093,154 | 3/1992 | Hatada | 427/333 |
| 5,143,750 | 9/1992 | Yamagata et al. | 427/302 |
| 5,225,274 | 7/1993 | Ogawa et al. | 428/333 |
| 5,238,746 | 8/1993 | Soga et al. | 428/420 |

FOREIGN PATENT DOCUMENTS

| | | |
|---|---|---|
| 0208218 | 1/1987 | European Pat. Off. . |
| 0363924 | 4/1990 | European Pat. Off. . |
| 0386784 | 9/1990 | European Pat. Off. . |
| 0484886 | 5/1992 | European Pat. Off. . |

OTHER PUBLICATIONS

World Patents Index, accession No. 90-062799, week 09, Derwent Publications Ltd., London, GB & JP-A-2 015101 (Matsushita Elec. Ind. K.K.), Jan. 18, 1990.

Primary Examiner—Diana Dudash
Attorney, Agent, or Firm—Fish & Richardson, P.C.

[57] ABSTRACT

A medical member having active hydrogen groups such as hydroxyl, amino or imino groups at its surface, is dipped, either directly or after formation of an inner layer on its surface, into a solution. The solution is prepared by dissolving a surface active material, e.g., $CF_3(CF_2)_7(CH_2)_2SiCl_3$ in a non-aqueous solvent. A dehydrochlorination reaction is brought about between active hydrogen groups at the surface of the member and SiCl groups of the surface active material, thus producing bonds of

$$CF_3(CF_2)_7(CH_2)_2Si(O\text{—})_3$$

over the entire surface. A fluorine-containing monomolecular film is formed, which is chemically (or covalently) bonded to the member surface and has a thickness at the nanometer level. Since the chemically adsorbed film is covalently bonded to the member or inner layer, it is chemically stable and difficult to separate. Medical members can be obtained when the invention is applied to an artificial tooth, a joint, a bone, a blood bag, a catheter, a blood transportation tool, a dialysis equipment part, an operation thread, a medical implant and an operation tool.

6 Claims, 4 Drawing Sheets

MEDICAL MEMBER AND METHOD OF MANUFACTURING THE SAME

This application is a division of U. S. application Ser. No. 08/089,629 filed Jul. 12, 1993, now U.S. Pat. No. 5,443,511, which is a continuation of U.S. application Ser. No. 07/824,314, filed Jan. 23, 1992, now abandoned.

BACKGROUND OF THE PRESENT INVENTION

This invention relates to medical members for insertion into organisms and, more particularly, to high performance medical members for insertion into organisms, typically prostheses such as an artificial heart and an artificial vein and medical devices such as a blood bag, a catheter, a blood transportation tool, dialysis apparatus, an artificial joint and an artificial tooth.

More specifically, the invention concerns an artificial joint, particularly an improved artificial joint featuring reduced frictional resistance.

DESCRIPTION OF THE PRIOR ART

Prostheses such as an artificial heart and an artificial vein and medical devices such as a blood bag, a catheter, a blood transportation tool, dialysis apparatus, an artificial joint and an artificial tooth are required to have very stringent properties such as having the capability of preventing blood agglomeration and being sanitary.

Heretofore, medical members for insertion into organisms such as artificial hearts are made inactive with respect to organisms in order to prevent thrombus or rejection.

In the prior art, however, there are various problems with the materials used in manufacturing the medical members.

The present invention seeks to solve the above problems inherent in the prior art. One object is therefore to provide a medical member for insertion into organisms, which is highly reliable and can prevent thrombus or rejection.

Artificial joints are mostly made of ceramics or metals. The choice of material depends upon type of organism, mechanical strength, frictional properties and so forth. Particularly, the surface of the artificial joint is finished to be as smooth as possible to improve the frictional property. For the frictional property improvement, usually a fluorine-based polymer coating film of polytetrafluoroethylene, for example, is used as an interface. There continues to be much research and investigation concerning the reduction of frictional resistance obtainable by using fluorine-based polymer coating films.

However, the fluorine-based polymer coating film which has been studied for reducing the frictional resistance, has a grave problem in that it poorly adheres to the substrate and is liable to be separated when its friction is brought about under application of a load, thus resulting in accumulation of its separate particles in the joint. For this reason, it has been the general practice to make the finish of the frictional part as smooth as possible and not adopt a means for positively reducing the frictional resistance.

SUMMARY OF THE INVENTION

It is an object of the invention to provide a high performance artificial joint, which can reduce frictional resistance, and a material for reducing frictional resistance which is not rubbed away even under application of a frictional load.

It is a further object of the invention to provide an artificial tooth, to which scale or unpleasant odor will not easily attach.

An objective of the invention is to provide a medical member comprising a chemically adsorbed film as a surface layer covalently bonded to the medical member by-Si-bonds, the chemically adsorbed film containing fluorocarbon chain groups.

It is preferable in this invention that the chemically adsorbed film is a monomolecular film.

It is preferable in this invention that the chemically adsorbed film is a polymer film.

It is preferable in this invention that the member is selected from the group consisting of an artificial tooth, an artificial joint, an artificial bone, a blood bag, a catheter, a blood transportation tool, a dialysis member, thread for operation, a medical implant and an operating tool.

It is preferable in this invention that the member is made of a material selected from the group consisting of ceramics, plastics, porcelains and metals.

It is preferable in this invention that the fluorine-containing chemically adsorbed film is laminated to a siloxane-based inner layer, the inner layer being bonded by covalent bonds to the surface of the material of the medical member, the inner layer and the chemically adsorbed film being bonded together by covalent bonds.

Another objective of this invention is to provide a method of manufacturing a medical member comprising the steps of contacting the medical member containing active hydrogen groups at the surface in a non-aqueous organic solution of a silane-based surface active material having a chlorosilane group at one end and a fluorocarbon group at the other end, thereby adsorbing the silane-based surface active material to the medical member, washing away non-reacted matter by using a non-aqueous solution, and reacting with water to obtain a medical member having a chemically adsorbed monomolecular film.

It is preferable in this invention that the active hydrogen group at the material surface is at least one functional group selected from the group consisting of a hydroxyl group, an imino group and an amino group.

It is preferable in this invention that the active hydrogen groups at the material surface are provided by a plasma or corona treatment.

Another objective of this invention is to provide the steps of contacting the medical member containing active hydrogen groups at the surface in a non-aqueous organic solution of a silane-based surface active material having a chlorosilane group at one end and a fluorocarbon group at the other end, thereby adsorbing the silane-based surface active material to the medical member, and then reacting with water to obtain a medical member having a chemically adsorbed polymer film.

Another objective of this invention is to provide the steps of contacting the medical member containing active hydrogen groups at the surface with a non-aqueous solution containing a material with the molecules thereof having a plurality of halosilyl groups, substituting silanol groups for the halosilyl groups in a portion of an inner layer formed on the surface of the medical member by reacting with water with or without preliminary removal of unreacted material on the surface by washing using a non-aqueous solution, contacting the medical member with active hydrogen groups at the surface in a non-aqueous organic solution containing a silane-based surface active material having a chlorosilane group at one end and a fluorocarbon group at the other end to adsorb the silane-based surface active material to the surface of the inner layer, washing away unreacted material by using a non-aqueous solution or without preliminary removal of unreacted material on the surface by washing with a non-aqueous solution, and reacting with water to form a laminated chemically adsorbed monomolecular film.

It is preferable in this invention that the material containing a plurality of halosilyl groups for forming the inner layer is at least one member of a group consisting of $SiCl_4$, $SiHCl_3$, $SiH_2Cl_2$, $Cl(SiCl_2O)_nCl_3$ where n represents an integer from 1 to 20.

BRIEF DESCRIPTION OF THE INVENTION

A medical member having active hydrogen groups such as hydroxyl, amino or imino groups at its surface, is dipped, either directly or after formation of an inner layer on its surface, into a solution. The solution is prepared by dissolving a surface active material, e.g., $CF_3(CF_2)_7(CH_2)_2SiCl_3$ in a non-aqueous solvent. A dehydrochlorination reaction is brought about between active hydrogen groups at the surface of the member and SiCl groups of the surface active material, thus producing bonds of over the entire surface. A fluorine-containing monomolecular film is formed, which is chemically (or covalently) bonded to the member surface and has a thickness at the nanometer level. Since the chemically adsorbed film is covalently bonded to the member or inner layer, it is chemically stable and difficult to separate. Excellent medical members can be obtained when the invention is applied to an artificial tooth, a joint, a bone, a blood bag, a catheter, a blood transportation tool, a dialysis equipment part, an operation thread, a medical implant and an operation tool.

According to the invention, a fluorocarbon-based monomolecular film having a super thin thickness at the nanometer level and biocompatible with organisms, is formed on the medical member surface. Thus, the medical member can be processed inserted into organisms without spoiling its intrinsic functions. It is thus possible to provide a highly reliable medical member for insertion into organisms, which can prevent thrombus and rejection. In addition, since The member is formed with a very thin surface layer containing carbon fluoride groups, it is inactive to blood and other body fluids. Further, The surface film is chemically bonded to the material by siloxane bonds, does not separate from the substrate and is excellent in durability.

Further, since the chemically adsorbed film according to the invention is a monomolecular film, it is thin, has excellent transparency and does not spoil the intrinsic properties of the medical member (i.e., the material).

Usual medical members are made of plastics, metals or ceramics, and are therefore inadequate for organisms. Accordingly, the surface of such material is oxidized in advance to be hydrophilic (for example by an oxygen plasma treatment at 100 W for about 30 minutes when the member is a plastic material such as a urethane resin) and then contacted with a non-aqueous solution containing molecules having a straight carbon chain having a chlorosilane ($-SiCl_nX_{3-n}$, n represents 1, 2 or 3. X represents a functional group) group at one end, e.g., a chlorosilane surface active material having a fluorocarbon group and a chlorosilane group.

According to the invention, the chemically adsorbed film is suitably formed by using a chlorosilane-based surface active material containing an alkyl fluoride group.

Examples of the chlorosilane-based surface active material containing an alkyl fluoride group are trichlorosilane-based surface active materials such as $CF_3(CF_2)_7(CH_2)_2SiCl_3$, $CF_3(CH_2)_2O(CH_2)_{15}SiCl_3$, $CF_3(CH_2)_2Si(CH_3)_2(CH_2)_{15}SiCl_3$, $F(CF_2)_4(CH_2)_2Si(CH_3)_2(CH_2)_9SiCl_3$, $CF_3COO(CH_2)_{15}SiCl_3$, $CF_3(CF_2)_5(CH_2)_2SiCl_3$, $F(CF_2)_8(CH_2)_2Si(CH_3)_2(CH_2)_9SiCl_3$, and lower-alkyl group substituted monochlorosilane- or dichlorosilane-based surface active materials such as $CF_3(CF_2)_7(CH_2)_2SiCl_n(CH_3)_{3-n}$, $CF_3(CF_2)_7(CH_2)_2SiCl_n(C_2H_5)_{3-n}$, $CF_3CH_2O(CH_2)_{15}SiCl_n(CH_3)_{3-n}$, $CF_3CH_2O(CH_2)_{15}SiCl_n(C_2H_5)_{3-n}$, $CF_3(CH_2)_2Si(CH_3)_2(CH_2)_{15}SiCl_n(CH_3)_{3-n}$, $F(CF_2)_4(CH_2)_2Si(CH_3)_2(CH_2)_9SiCl_n(C_2H_5)_{3-n}$, $F(CF_2)_8(CH_2)_2Si(CH_3)_2(CH_2)_9SiCl_n(CH_3)_{3-n}$, $CF_3COO(CH_2)_{15}SiCl_n(CH_3)_{3-n}$, and $CF_3(CF_2)_5(CH_2)_2SiCl_n(CH_3)_{3-n}$ (where n represents 1 or 2). Among these materials, trichlorosilane-based surface active materials are particularly suitable. This is so because chlorosilyl bonds other than those bonded to their hydrophilic groups form inter-molecular bonds between adjacent chlorosilane and siloxane bonds, thus permitting formation of a stronger chemically adsorbed film. Further, where n represents an integer most suitably ranging from about 3 to about 25, is suitable because of balance with such functions as being soluble in solvents, able to be chemically adsorbed and water-repelling, oil-repelling, and anti-contaminating. Further, by incorporating an ethylene or acetylene group in an alkyl fluoride chain portion, the chemically adsorbed film can be corsslinked after its formation by irradiating it with an electron beam of 5 Mrad. to further improve the hardness.

The chlorosilane-based surface active material capable of use according to the invention is not limited to those in the form of a straight chain as noted above, and it is possible to use those in a form having a branched alkyl fluoride or hydrocarbon group or those in a form having a substituted alkyl fluoride or hydrocarbon group for silicon at one end (i.e., those represented by a formula $R_2SiCl_2$, $R_3SiCl$, $R^1R^2SiCl_2$ or $R^1R^2R^3SiCl$ where R, $R^1$, $R^2$ and $R^3$ represents an aklyl fluoride or hydrocarbon group. To increase the adsorption density, however, the straight chain form is preferred.

Further, by chemically adsorbing a material for forming an inner layer material having a plurality of chlorosilyl groups, e.g., $SiCl_4$, $SiHCl_3$, $SIH_2Cl_2$, and $Cl(SiCl_2O)_nCl_3$ (where n represents an integer in a range from 1 to 20), $SiCl_m(CH_3)_{4-m}$, $SiCl_m(C_2H_5)_{4-m}$ (where m represents 1, 2 or 3), and $HSiCl_1(CH_3)_{3-1}$, $HSiCl_1(C_2H_5)_{3-1}$ (where 1 represents 1 or 2), and then reacting the material with water, chlorosilyl bonds at the surface are converted to hydrophilic silanol bonds. This means that when a plastic molding is the process material, the surface thereof can be made hydrophilic.

Among the medical members able to be fitted in organisms according to the invention, there are prostheses such as artificial hearts and artificial veins and also such members as blood bags, catheters, blood transportation tools and medical parts used for dialysis equipment. In examples given below, artificial veins are specifically described.

According to the invention, the problems inherent in the prior art are solved with an artificial joint, which is provided with a fluorine-containing chemically adsorbed film formed on its surface.

According to the invention, a chemically adsorbed film of fluorocarbon-based molecules having a super thin thickness at the nanometer level is formed on the surface of an artificial joint. Thus, the fluorocarbon-based molecule film can reduce frictional resistance. In addition, since it is a chemically adsorbed film, it is firmly bonded to the processed material and is difficult to separate. Further, since it is thin and it does not spoil the functions intrinsic to the artificial joint.

For usual artificial joints, ceramics or metals are used substantially exclusively from the considerations of the mechanical strength and moldability. However, hard plastics are also used. Therefore, the surface of such artificial joints contains hydroxyl or like hydrophilic groups having active hydrogen. Therefore, usually a chlorosilane-based surface active material having a chlorosilyl group at one end and fluorocarbon at the other end can be readily chemically adsorbed. With an artificial joint made of such material as stainless steel or like metal or hard plastic which can be difficult to oxidize, the surface may be made hydrophilic in advance by means of a plasma or corona treatment. Further, where the density of hydrophilic groups is low, a material containing a plurality of chlorosilyl bonds may be chemically adsorbed to form a coating film of this material, then the chlorosilyl bonds may be converted into silanol bonds by reacting with water, and then the chlorosilane-based surface active material may be laminated to the silanol bonds. In this way, a high density fluorocarbon-containing, chemically adsorbed film may be obtained. This method of preliminarily forming a chemically adsorbed film of a material containing a plurality of chlorosilyl bonds, is of course applicable not only to cases of low hydrophilic group density but also to any process material. Further, the method of preliminarily chemically adsorbing a material containing a plurality of chlorosilyl bonds, does not only improve but also permits control of the density of adsorption of chlorosilane-based surface active material. The chemically adsorbed film provided for an artificial joint according to the invention can sufficiently fulfill its function even if it is a monomolecular film. A single chemically adsorbed monomolecular film may be formed without any specific contrivance. That is, it may be formed by contacting the artificial joint with the chlorosilane-based surface active material and then washing the material with a non-aqueous solution. Further, a single chemically adsorbed film of a material containing a plurality of chlorosilyl bonds is sufficiently effective. Again in this case, a chemically adsorbed monomolecular film may be formed by washing with a non-aqueous solution, as noted above. The artificial joint according to the invention is sufficiently effective so long as a chlorosilane-based surface active material is chemically adsorbed to at least a joint section, and there is no need of forming any chemically adsorbed film on any unnecessary part. To cause selective adsorption of a chemically adsorbed film, only the necessary part may be dipped in a chlorosilane-based surface active material solution. With such selective formation of chemically adsorbed film, the frictional resistance can be reduced without sacrifice of fitness to organisms.

Among these examples, those based on trichlorosilane are particularly suitable, because chlorosilyl groups other than those bonded with their hydrophilic groups form intermolecular bonds between adjacent chlorosilane groups and siloxane bonds, thus permitting formation of a firmer chemically adsorbed monomolecular film. Further, by incorporating a C=C or C≡C group into an alkyl chain or alkyl fluoride chain portion, the chemically adsorbed film can be crosslinked after formation by irradiating it with an electron beam of about 5 Mrads to further improve the hardness.

The artificial joint according to the invention may be manufactured by merely dipping and folding the artificial joint following the formation process in a non-aqueous solution containing a chlorosilane-based surface active material. No other specific step is required.

Examples of the solvent to be used according to the invention are hexadecane, toluene, xylene, dicyclohexyl, carbon tetrachloride, chloroform freon-113 and other non-aqueous organic solvents.

Typical artificial joints according to the invention are those of the knee, finger, jaw, shoulder, arm, wrist, ankle, crotch, etc. In the examples given hereinafter, the knee is described.

Further, by processing the surface of an artificial tooth in the same method, the processed artificial tooth has its surface covered by a very thin inactive coating film containing fluorocarbon groups, in which scale or unpleasant odor will not easily attach.

As shown, since a fluorocarbon-based monomolecular film having a thickness at the nanometer level is formed on the surface of a medical member for insertion into organisms, the intrinsic functions of the medical member are not spoil. In addition, the carbon fluoride-based monomolecular film is quite inactive to organisms and dose not separate or wear out. Thus, the film is very useful for medical members, which are required to prevent thrombus or rejection.

Further, with the artificial joint provided with a fluorine-containing chemically adsorbed film, a fluorocarbon-based molecular film having a thickness at the nanometer level can be formed on the surface of a frictional part of the artificial joint without spoiling the intrinsic functions of the artificial joint. The carbon fluoride-based chemically adsorbed film is biocompatible with respect to organisms, permits enhanced reduction of frictional resistance and dose not separate or wear out. Thus, the film is very useful for an artificial joint which is to be used in organisms, and in which lubricant or the like can not be used.

Further, by covering the surface of an artificial tooth by the same method, it is possible to prevent attachment of scale, anti-contaminants and/or unpleasant odor.

EXAMPLE 1

Figure 1:
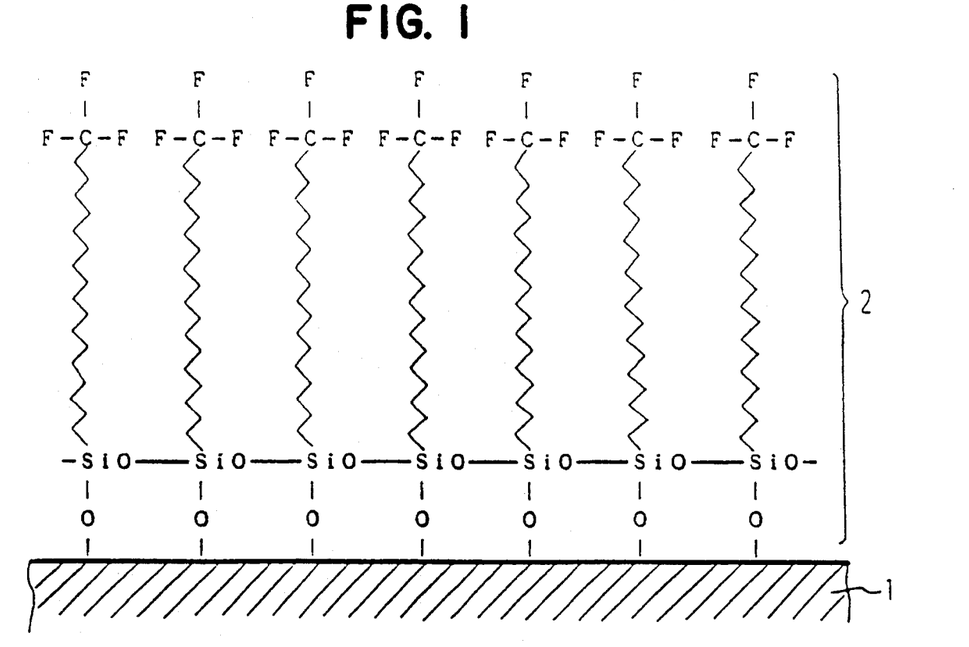
FIG. 1 is a schematic sectional view, enlarged to a molecular level, showing the surface of an artificial vein as in example 1 of the invention.

A processed artificial blood vessel (vein) made of a polyethylene (or a plastic material such asurethane resin, nylon, silicon resins or PVA resins) is prepared. Its surface is made hydrophilic by treating in an oxygen-containing plasma atmosphere at 100 W for about 30 minutes. As an alternative method of making the surface hydrophilic, the processed artificial vein is dipped and held for 30 minutes in a solution. The solution is obtained by adding 10 wt. % of potassium dichlomate in concentrated sulfuric acid at 80° C. The artificial vein can also be dipped and held for one hour in a solution which is obtained by dissolving 10 wt. % of potassium perchlorate in concentrated sulfuric acid. It is not necessary, however, to surface treat plastics having imino (=NH) groups such as polyamide or polyurethane substrates. Because imino groups have active hydrogen, it is relatively easy to reduce the groups by initiating the dehydrochlorination reaction with the chlorosilyl groups of the surface active material. Then, the artificial vein is washed with an organic solvent and dipped and held for about 2 hours in a non-aqueous solution containing a material having a fluorocarbon group and a chlorosilane group, e.g., a solution obtained by dissolving about 1 wt. % of $CF_3(CF_2)_7(CH_2)_2SiCl_3$ in a freon-113 solution. As a result, a hydrochloric acid removal reaction (dehydrochlorination reaction) is brought about between the —SiCl groups of the material having a fluorocarbon group and a chlorosilane group and hydroxyl groups numerously contained at the plasma-treated surface (or a plastic or metal surface), thus producing bonds of $CF_3(CF_2)_7(CH_2)_2Si(O—)_3$ over the entire surface. It was found that a fluorine-containing monomolecular film 2 was formed. The film was chemically bonded to the surface 1 and had a thickness of about 1.5 nanometers (FIG. 1). The monomolecular film was chemically bonded very firmly and did not separate.

This monomolecular film consisted of fluorine-containing molecules in an array on the surface. It was biocompatible with inactive to organisms and did not spoil the elasticity and other physical properties of the coated articles. It is of course very effective for such medical members as a blood bag and a catheter.

Figure 2:
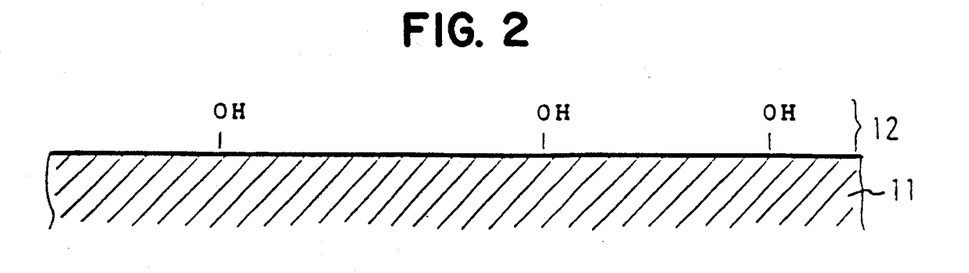
FIG. 2 is a schematic sectional view, enlarged to a molecular level, showing the surface of a medical member as in example 2 of the invention.

EXAMPLE 2

Where a fluorocarbon-based monomolecular film is to be formed at a high density compared to that of EXAMPLE 1, a member having been plasma treated is dipped and held for about 30 minutes in a solution. The solution is prepared by dissolving 1 wt. % by weight of a material containing a plurality of chlorosilyl groups, e.g., $SiCl_4$, $SiHCl_3$, $SiH_2Cl_2$, and Cl $(SiCl_2O)_nCl_3$ (where n represents an integer in a range from 1 to 20), particularly $SiCl_4$, which is relatively small and highly active with respect to hydroxyl groups, thus being greatly effective in making the member surface uniformly hydrophilic. As a result, a dehydrochlorination reaction is brought about on the surface of the member 11 owing to hydrophilic —OH groups 12 provided at the surface by the plasma treatment (FIG. 2). A chlorosilane monomolecular film of a material containing a plurality of trichlorosilyl groups can then be formed.

As an example, by using $SiCl_4$ as the material containing a plurality of trichlorosilyl groups, a hydrochloric acid removal reaction (dehydrochlorination reaction) was brought about on the surface of the member 11 owing to a small amount of exposed hydrophilic —OH groups. Thus, molecules represented by the formulas 1 and/or 2:

were secured to the surface via —SiO— bonds.

Figure 3:
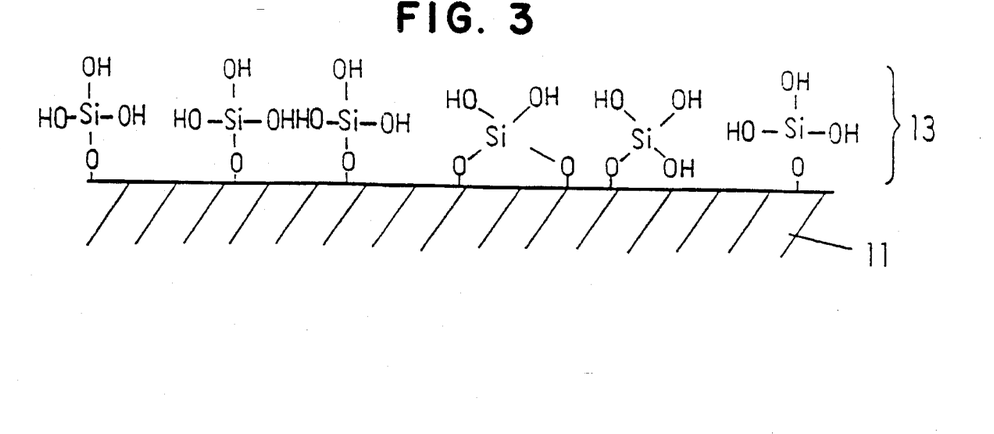
FIG. 3 is a schematic sectional view, enlarged to a molecular level, showing the surface of the medical member having a siloxane monomolecular film.

By subsequently washing the member with a non-aqueous solvent, e.g., freon-113, and then with water. $SiCl_4$ molecules unreacted with the member surface were removed, thus obtaining on the member surface a siloxane monomolecular film 13 as represented by formulas 3 and/or 4:

The monomolecular film 13 thus formed was perfectly bonded to the member surface via chemical bonds of —SiO— and do not separate (FIG. 3).

Figure 4:
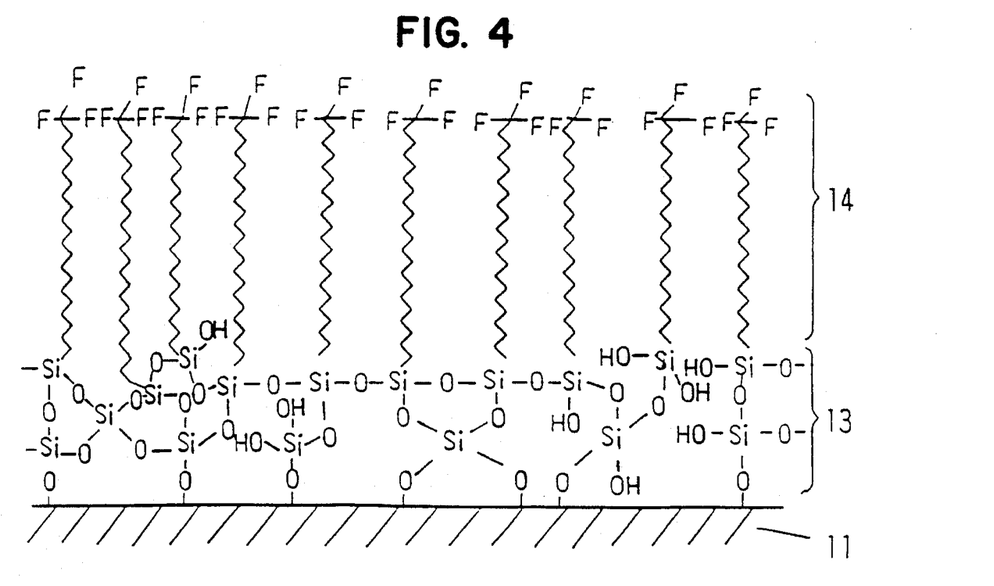
FIG. 4 is a schematic sectional view, enlarged to a molecular level, showing the surface of the medical member after formation of a fluorine-coating monomolecular film.

Then, the member was dipped and held for about 1 hour in a non-aqueous solution. The solution contained a material having a fluorocarbon group and a chlorosilane group, e.g., a solution was obtained by dissolving about 3 wt. % of $CF_3(CF_2)_7(CH_2)_2SiCl_3$ in a freon-113 solution. As a result, a hydrochloric acid removal reaction (dehydrochlorination reaction) is brought about between —SiCl groups of the material having a fluorocarbon group and a chlorosilane group and hydroxyl groups at the member surface (e.g., a plastic or metal surface), thus producing bonds of $CF_3(CF_2)_7(CH2)_2Si(O—)_3$ over the entire surface. It was found that a fluorine-containing monomolecular film 14 was formed. The film was chemically bonded to the surface 11 and had a thickness of about 1.5 nanometers (FIG. 4). The monomolecular film was chemically bonded very firmly and did not separate.

While the above example used $CF_3(CF_2)_7(C_2)_2SiCl_3$ as the fluorocarbon-based surface active material, by adding or incorporating ethylene or acetylene group into an alkyl chain portion, the monomolecular film can be crosslinked after formation by irradiating it with an electron beam of about 5 Mrads, and thus it is possible to further improve the hardness of the monomolecular film.

Further, by adsorbing a mixture of two different surface active materials having different molecular lengths, e.g., $CF_3(CF_2)_7(CH_2)_2Si(CH_3)_2(CH_2)_9SiCl_3$ and $CF_3(CF_2)_7(CH_2)_2Si(CH_3)_2(CH_2)_6SiCl_3$ or $CF_3(CF_2)_7(CH_2)_2SiCl_3$ and $CF_3(CF_2)_5(CH_2)_2SiCl_3$ in a ratio of 3:1 to 1:3, the member surface may be made irregular at the molecular level, thus further improving the water- and oil-repelling properties and further enhancing the effect of thrombus prevention.

EXAMPLE 3

Figure 5:
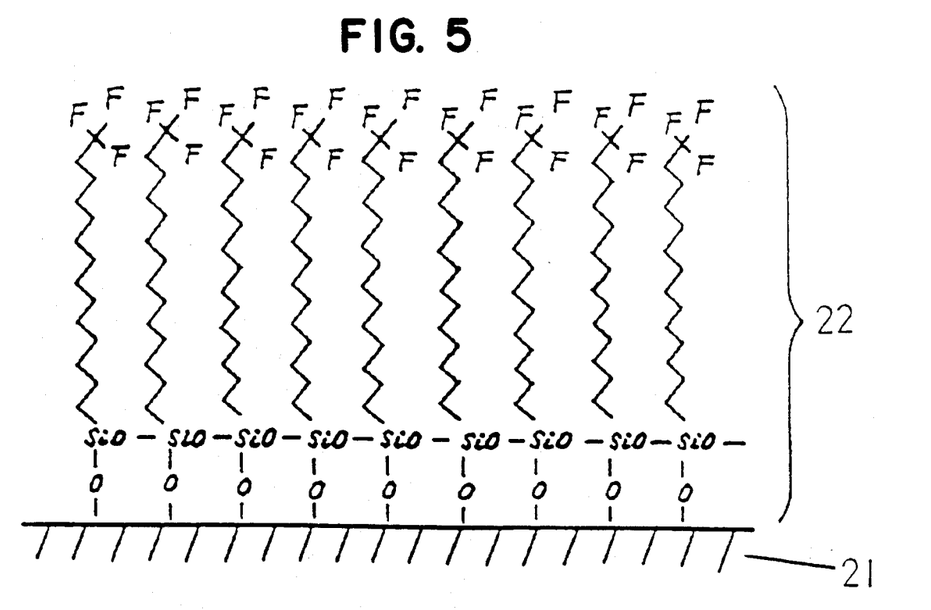
FIG. 5 is a schematic sectional view, enlarged to a molecular level, showing the surface of an artificial joint as in example 5 of the invention.

A processed alumina knee joint 21 was washed with an organic solution, and then only its joint part was dipped and held for about 2 hours in a solution. The solution was prepared by dissolving 10 wt. % of a material containing a carbon fluoride group and a chlorosilane group, e.g., $CF_3(CF_2)_7(CH_2)_2SiCl_3$ in a solution containing 80 wt. % of n-hexadecane, 12 wt. % of carbon tetrachloride and 8 wt. % of chloroform. As a result, a dehydrochlorination reaction was brought about between —SiCl groups of the surface active material having a fluorocarbon group and a chlorosilyl group and hydroxyl groups numerously contained at the alumina surface of the joint part of the knee joint 21, thus producing bonds represented by formula 5 at the film surface. The film was then washed with chloroform to remove unreacted material remaining on the surface, followed by washing with water or exposing to air containing moisture. The —SiCl group was changed to a —SiOH group as the formula [6].

Each silanol group (—SiOH) was then dehydrated and crosslinked to form a siloxane bond (—SiO—) after drying as in the formula [7]. Drying temperature may be room temperature or above.

The adsorbed monomolecular film 22 has a fluorine group and is chemically bonded (i.e., covalently bonded) to the joint substrate 21. The formation of chemically adsorbed monomolecular film 22 was measured by FTIR spectrometry and the thickness was about 1.5 nanometers (nm). The monomolecular film was very firmly chemically bonded and did not separate.

With a joint of a metal such as stainless steel or palladium other than alumina, a similar monomolecular film could be formed by merely adjusting the adsorption time because the surface is covered with a natural oxide film naturally containing hydroxyl groups.

This joint was tested by carrying out a sliding operation about 10,000 times. It was found that the frictional resistance could be greatly reduced compared to a non-processed joint. The monomolecular film did not separate, and no scar or scratch was produced.

EXAMPLE 4

Figure 6:
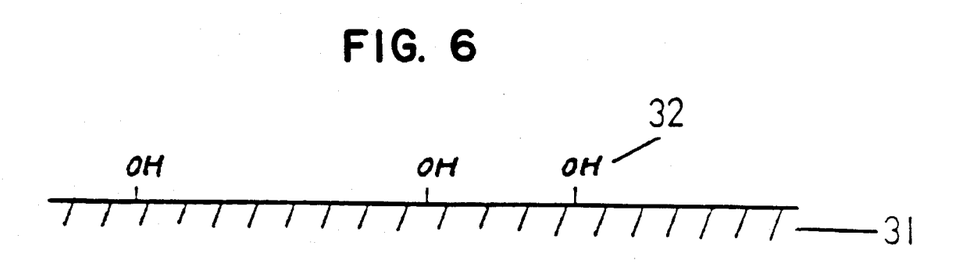
FIG. 6 is a schematic sectional view, enlarged to a molecular level, showing the surface of a further embodiment of the artificial joint as in example 4 of the invention.

As shown in FIG. 6, a stainless steel joint 31, which was hydrophilic but contained less hydroxyl groups, was dipped and held for 30 minutes in a solution. The solution was obtained by dissolving 1 wt. % by weight as $SiCl_4$ of a material having a plurality of chlorosilyl bonds in a chloroform solvent. As a result, a dehydrochlorination reaction was brought about on the surface of the knee 31 owing to a certain amount of hydrophilic —OH groups 32 present in the frictional part of the metal joint 31. By dipping the chemically adsorbed film thus obtained in a non-aqueous solvent, i.e., carbon tetrachloride, $SiCl_4$ unreacted with the joint 31 was washed away, thus obtaining a chemically adsorbed monomolecular film as represented above formulas 1 and/or 2 on the surface of the knee 31.

Figure 7:
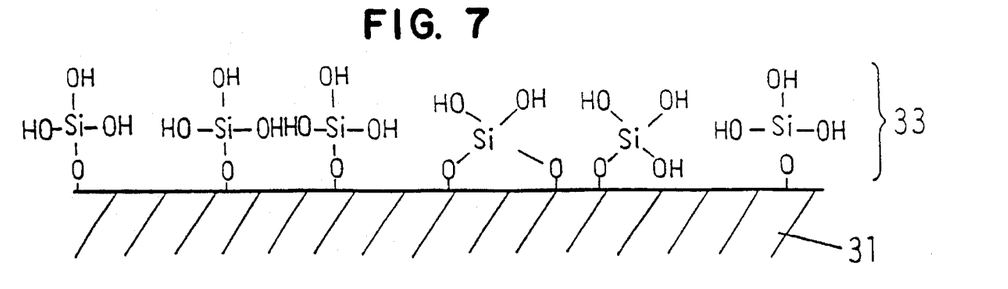
FIG. 7 is a schematic sectional view, showing the surface of the artificial joint provided with a chemically adsorbed film containing a plurality of silanol bonds as in example 4 of the invention.

By subsequently dipping the joint in water, a siloxane monomolecular film 33 having a plurality of silanol groups as represented above by formulas 3 and/or 4 could be obtained on the surface of the frictional part of the joint 31, as shown in FIG. 7.

The siloxane monomolecular film 33 thus formed was perfectly bonded via chemical bonds of —SiO— and did not separate. It contained numerous —SiOH bonds at the surface, the bonds corresponding in number to about three times the initial number of hydroxyl groups.

Figure 8:
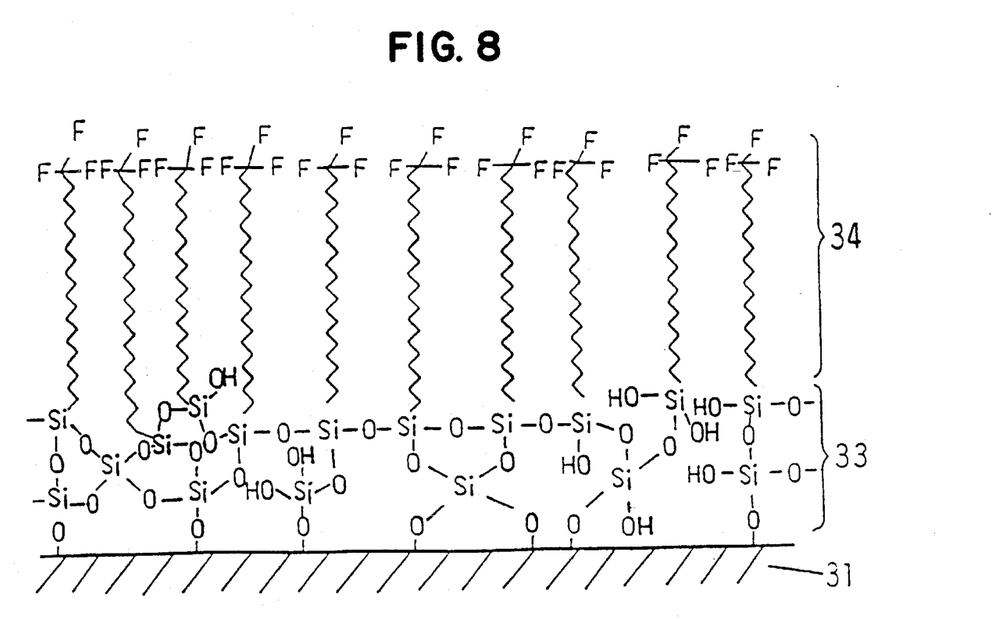
FIG. 8 is a schematic sectional view, enlarged to a molecular level, showing the surface of a further embodiment of the artificial joint as in example 4 of the invention.

In a further example, as in EXAMPLE 3, the frictional part of the joint 31 provided with the monomolecular film 33 containing numerous —SiOH bonds was dipped and held in a solution. The solution was obtained by dissolving a chlorosilane-based surface active material in a non-aqueous solution. As a result, bonds as represented above formulas 5 to 7 were produced on the surface of the frictional part of the joint. A fluorine-containing chemically adsorbed film 34 was thus obtained, as shown in FIG. 8. The film was chemically bonded to the inner siloxane monomolecular film 33 over the entire surface of the frictional part of the joint 31. It had a high density, and its thickness was about 1.5 nanometers.

The chemically adsorbed film 34 did not separate in a peel-off test. The frictional resistance was reduced to one half compared to the frictional part of a joint, on which a fluorine-containing monomolecular film was directly formed.

EXAMPLE 5

A solution was prepared by using $CF_3(CF_2)_9(CH_2)_2—SiCl_3$ as a silane surface active material and dissolving the same in freon 113 to a concentration of 2 wt. % A tooth as a ceramic (porcelain) substrate was dipped and held into this solution at room temperature for one hour. The substrate was washed by "Fluorinert FC72" (products by 3M corp., fluorin-based solution). Since the surface of the substrate contained hydroxyl groups, a reaction between the chlorosilyl groups of the chlorosilane-based surface active material and the hydroxyl groups occurred as represented in the formula [8]. This reaction proceeded substantially the same as above in formulas [5] to [7].

Formula [8]

An adsorbed monomolecular film was obtained on the surface of the ceramic tooth surface. The adsorbed monomolecular film has a fluorine group and is chemically bonded (i.e., covalently bonded) to the tooth surface. The chemical bond is via a —SiO— covalent bond. This chemically adsorbed monomolecular film was measured by FTIR spectrometry and the thickness was about 1.5 nanometers (nm). It is firmly bonded such that it will not separate.

The treated ceramic tooth was compared to an unreacted or untreated ceramic tooth. The treated ceramic tooth greatly reduced contaminant (i.e., scale) adherence. In addition, any contaminant which did remain on the treated ceramic tooth could be readily removed by wiping with a brush or the like. This could be done without causing any scar or scratch on the ceramic tooth surface.

The above washing step with the "Fluorinert FC72" was omitted, and a fluorocarbon polymer film was adsorbed to the ceramic tooth. The fluorocarbon-based polymer film was in satisfactorily close contact with the ceramic tooth. The film was substantially pin-hole free, thin, anti-contaminating, transparent and brilliant.

EXAMPLE 6

A processed artificial plastic tooth made of poly(methyl methacrylate) (PMMA) resin is prepared. Its surface is made hydrophilic by treating in an oxygen-containing plasma atmosphere at 100 W for about 30 minutes. Then it was dipped and held for about 30 minutes in a solution. The solution was prepared by dissolving 1 wt. % by weight of $Cl(SiCl_2O)_3Cl_3$ (inner layer adsorbed material), which is relatively small and highly active with respect to hydroxyl groups, thus having a great effect upon making the member surface uniformly hydrophilic. As a result, a dehydrochlorination reaction is brought about on the surface of the PMMA tooth owing to hydrophilic —OH groups provided to the surface. A chlorosilane monomolecular film of a material containing a plurality of trichlorosilyl groups can then be formed.

As an example, by using the material containing a plurality of trichlorosilyl groups, a hydrochloric acid removal reaction (dehydrochlorination reaction) was brought about on the surface of the PMMA tooth owing to a small amount of exposed hydrophilic —OH groups. Thus, molecules represented by the formulas 9 and/or 10:

[Formula 9]

[Formula 10]

were secured to the surface via —SiO— bonds.

By subsequently washing the member with a non-aqueous solvent, e.g., freon-113, and then with water, molecules unreacted with the PMMA tooth surface were removed, thus obtaining on the member surface a siloxane monomolecular film as represented by formulas 11 and/or 12:

[Formula 11]

[Formula 12]

The monomolecular film thus formed was perfectly bonded to the PMMA tooth surface via chemical bonds of —SiO— and did not separate.

The above washing step with the freon-113 was omitted, and a siloxane-based inner polymer film was adsorbed to the PMMA tooth. The inner polymer film was in satisfactorily close contact with the PMMA tooth surface.

Then, the member was dipped and held for about 1 hour in a non-aqueous solution. The solution contained a material having a fluorocarbon group and a chlorosilane group, e.g., a solution was obtained by dissolving about 2 wt % of in a freon-113solution As a result, a hydrochloric acid removal reaction (dehydrochlorination reaction) is brought about between —SiCl groups of the material having a fluorocarbon group and a chlorosilane group and hydroxyl groups at inner layer surface, thus producing bonds of over the inner layer surface. It was found that a fluorine-containing monomolecular film was formed. The film was chemically bonded to the surface and had a thickness of about 1.5 nanometers. The monomolecular film was chemically bonded very firmly and did not separated.

The above washing step with the freon-113 was omitted, and a fluorocarbon polymer film was adsorbed to the PMMA tooth via an inner layer. The fluorocarbon-based polymer film was in satisfactorily close contact with the PMMA tooth. The film was substantially pin-hole free, thin, anti-contaminating, transparent and brilliant.

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim:

1. A method of manufacturing a medical member comprising the steps of contacting a medical member containing active hydrogen groups at the surface in a nonaqueous organic solution of a silane-based surface active material having a chlorosilane group at one end and a fluorocarbon group at the other end, thereby adsorbing said silane-based surface active material to said medical member, washing away non-reacted matter by using a non-aqueous solution, and reacting with water to obtain a medical member having a chemically adsorbed monomolecular film.

2. The method of manufacturing a medical member according to claim 1 wherein the active hydrogen group at the material surface is at least one functional group selected from the group consisting of a hydroxyl group, an imino group and an amino group.

3. The method of manufacturing a medical member according to claim 1, wherein said active hydrogen groups at the material surface are provided by a plasma or corona treatment before the contacting step.

4. A method of manufacturing a medical member comprising the steps of contacting a medical member containing active hydrogen groups at the surface in a non-aqueous organic solution of a silane-based surface active material having a chlorosilane group at one end and a fluorocarbon group at the other end, thereby adsorbing said silane-based surface active material to said medical member, and then reacting with water to obtain a medical member having a chemically adsorbed polymer film.

5. A method of manufacturing a medical member comprising a chemically adsorbed mono-molecular film, said method comprising the sequential steps of contacting a medical member containing active hydrogen groups at its surface with a non-aqueous solution containing a material comprising a plurality of molecules with the molecules thereof having a plurality of halosilyl groups in a portion of an inner layer formed on the surface of said medical member by reacting with water with or without preliminary removal of unreacted material on the surface by washing using a non-aqueous solution, wherein said inner layer comprises a surface, contacting said medical member with active hydrogen groups at the surface in a non-aqueous organic solution containing a silane-based surface active material having a chlorosilane group at one end and a fluorocarbon group at the other end to adsorb said silane-based surface active material to the surface of said inner layer, washing away unreacted material by using a non-aqueous solution or without preliminary removal of unreacted material on the surface by washing with a non-aqueous solution, and reacting with water thereby forming a medical member comprising a chemically adsorbed monomolecular film.

6. The method of manufacturing a medical member according to claim 5, wherein said material containing a plurality of halosilyl groups for forming said inner layer is at least one member of a group consisting of $SiCl_4$, $SiHCl_3$, $SiH_2Cl_2$, $Cl(SiCl_2O)_nCl_3$ where n represents an integer from 1 to 20.

* * * * *